US005795314A

United States Patent [19]

Berenstein

[11] Patent Number: 5,795,314

[45] Date of Patent: Aug. 18, 1998

[54] THERAPEUTIC FINGERNAIL TREATMENT DEVICE

[76] Inventor: Moshe Berenstein, 1/7 Janus Korczak St., Netanya, Israel

[21] Appl. No.: 665,864

[22] Filed: Jun. 19, 1996

[51] Int. Cl.[6] .......... A61M 35/00; A45D 29/18

[52] U.S. Cl. .......... 601/166; 132/74.5; 604/292

[58] Field of Search .......... 132/73, 73.5, 74.5, 132/285; 601/11, 166, 160; 604/292, 293, 316; 134/198, 200

[56] References Cited

U.S. PATENT DOCUMENTS

| | | | |
|---|---|---|---|
| 1,399,095 | 12/1921 | Webb, Sr. | 601/11 |
| 1,715,043 | 5/1929 | Oye | 601/166 |
| 2,722,224 | 11/1955 | Blann | 132/88.5 |
| 3,088,459 | 5/1963 | Rabinoff | 601/166 |
| 3,943,951 | 3/1976 | Spotz | 134/200 |
| 4,020,856 | 5/1977 | Masterson | 132/74.5 |
| 4,258,734 | 3/1981 | Hehlo | 132/74.5 |
| 4,289,152 | 9/1981 | Fuhre | 132/74.5 |
| 4,307,738 | 12/1981 | Barns | 132/74.5 |
| 4,635,656 | 1/1987 | Daniel | 132/75 |
| 4,742,836 | 5/1988 | Buehler | 134/182 |
| 5,098,415 | 3/1992 | Levin | 604/293 |

FOREIGN PATENT DOCUMENTS

| | | | |
|---|---|---|---|
| 2100598 | 1/1983 | United Kingdom | 132/74.5 |

*Primary Examiner*—Todd E. Manahan
*Attorney, Agent, or Firm*—Edward Langer

[57] ABSTRACT

A therapeutic fingernail treatment device which injects active ingredients via a specially-designed nozzle, to remedy fingernail fungus infections. In a preferred embodiment, the device is constructed as a spray nozzle which attaches to the fingernail, and which is enclosed in a sleeve sealed around the fingernail. By developing cyclical high and low pressure conditions in the sleeve, active ingredients are injected into the space between the fingernail and the fingertip, to achieve the desired therapeutic effects. Thus, fingernail fungus infections can be treated and eliminated. Advantages of the invention include conservation of the usage of active ingredients by recycling them, contrary to existing techniques. The use of a sealed sleeve eliminates wastage of ingredients. The provision of a contoured spray nozzle insures increased efficiency by providing good contact between the active ingredients and the entire fingernail area. In addition, the pressure developed within the sealed sleeve affords good impregnation of the active ingredients within the affected area. A compact design can be provided, and no special skill is required for device operation.

15 Claims, 3 Drawing Sheets

THERAPEUTIC FINGERNAIL TREATMENT DEVICE

FIELD OF THE INVENTION

The present invention relates to personal care accessories and medical devices, and more particularly, to a device for treating skin fungus infections under the fingernail.

BACKGROUND OF THE INVENTION

Fungi are among the strongest and most durable organism groups. They are capable of growing in almost any place including the human body. When one or more of the fingernals or toenails is infected with them, the result is the fungus infection known as onychomycosis, which is primarily responsible for tinea pedis, or fungal infection of the feet.

Recent research in the United States proves that at least three percent of the general population suffers from fungus infections and the frequency of infections is on the rise. This type of infection can cause skin deformation and painful complications, and can lead to the development of secondary infections and pressure sensitivity in the fingers. In addition, there is a social aspect, since non-treatment of the fingernail contributes to spread of infections and injury to a large number of individuals.

Various fingernail cleaning and personal care devices are known, including that described in U.S. Pat. No. 4,742,836 to Buehler, which describes a receptacle having a small diameter fluid passageway, to avoid spraying out the fluid retained in it during a cleaning operation. In U.S. Pat. No. 4,635,656 to Daniel, there is described a fingernail cleaning device having a cylindrical tubular housing with an orifice disc providing a splash guard.

In U.S. Pat. No. 4,307,738 to Barns, there is described a vibrating, heated nail bath for soaking fingernails prior to manicuring. A description is given of various solutions for use in softening the skin and providing a bactericidal effect.

In U.S. Pat. No. 4,289,152 to Fuhre, there is disclosed a fingernail cleaning apparatus in a housing with an aperture for inserting a finger. A pump mounted on the housing causes discharge of liquid via a nozzle formed with a projection for pushing the skin near the fingertip away from the fingernail when the fingertip is pressed against the nozzle member.

A personal care appliance useful as a manicure device is described in U.S. Pat. No. 4,258,734 to Hehlo, and is constructed with a water jet nozzle to supply liquid under pressure, and a spray shield in which a finger may be inserted for cleaning.

In U.S. Pat. No. 4,020,856 to Masterson, a fingernail and hand cleaning apparatus applies pulsating jets of liquid to the ends of the fingers, while the hand is seated in a hand rest.

U.S. Pat. No. 2,722,224 to Blann discloses a dispenser for fingernail treating liquid, which sprays a fingernail with polish or other treatment liquids via a spray nozzle on a pressurized canister-type dispenser.

The particular problems associated with treating the fingernail against fungus have not been successfully addressed by the prior art fingernail cleaning and manicuring devices.

Therefore, it would be desirable to provide a device and method for treating fingernail fungus in a novel fashion.

SUMMARY OF THE INVENTION

Accordingly, it is a principal object of the present invention to overcome the disadvantages associated with prior art methods and devices and provide a therapeutic fingernail treatment device which injects active ingredients via a specially-designed nozzle, to remedy fingernail fungus infections.

In accordance with a preferred embodiment of the present invention, there is provided a therapeutic fingernail treatment device comprising:

means for enclosing a fingernail in sealed fashion; and nozzle means attached at an end of said enclosing means and facing said fingernail, said nozzle means being connected to a fluid source having means for reversibly pumping said fluid therethrough, and back to said fluid source, in cyclical fashion, such that said fluid periodically flows under said fingernail, and is withdrawn therefrom, providing therapeutic fingernail treatment.

In a preferred embodiment, the device is constructed as a spray nozzle which attaches to the fingernail, and which is enclosed in a sleeve sealed around the fingernail. By developing cyclical high and low pressure conditions in the sleeve, active ingredients are injected into the space between the fingernail and the fingertip, to achieve the desired therapeutic effects. Thus, fingernail fungus infections can be treated and eliminated.

The present invention provides advantages over existing devices, especially since it conserves the usage of active ingredients by recycling them, contrary to existing techniques. The use of a sealed sleeve eliminates wastage of ingredients.

The provision of a contoured spray nozzle insures increased efficiency by providing good contact between the active ingredients and the entire fingernail area. In addition, the pressure developed within the sealed sleeve affords good impregnation of the active ingredients within the affected area.

The invention can be provided in a compact design, and its operation does not require any special skill.

Other features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF A PREFERRED EMBODIMENT

Figure 1:
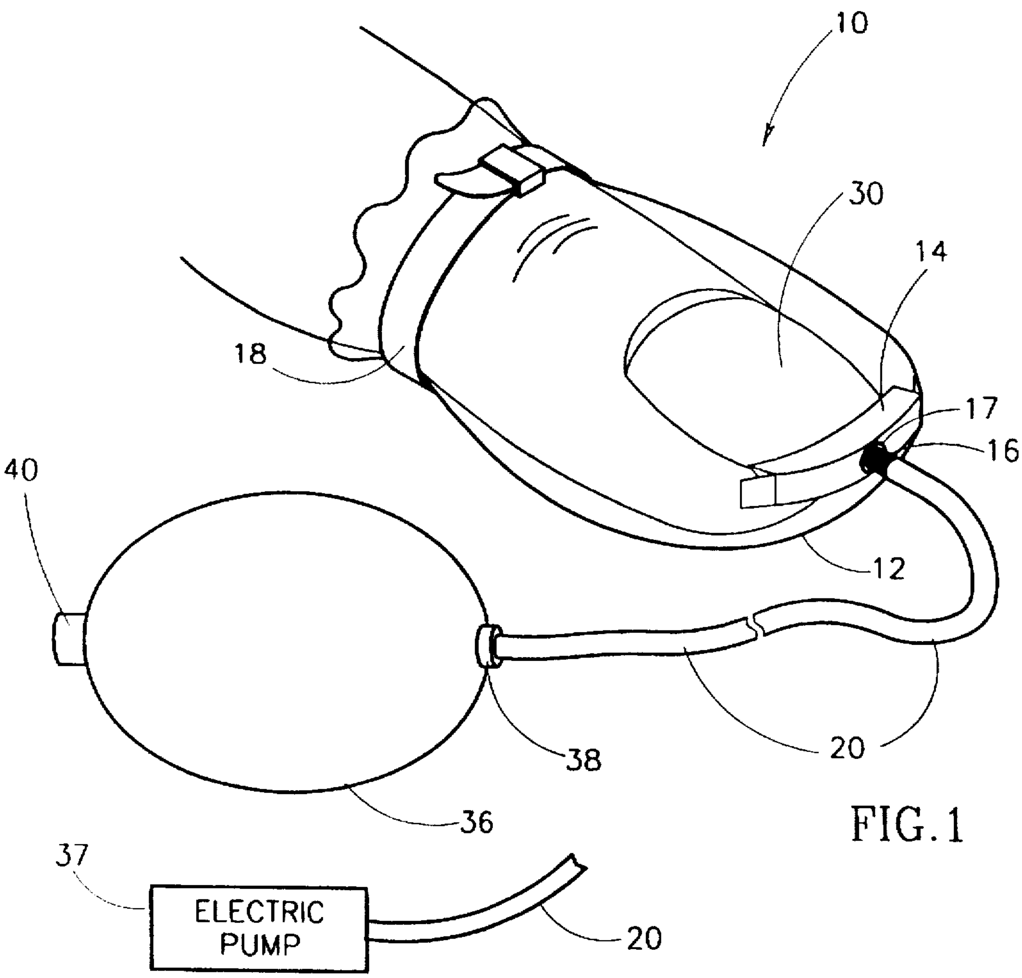
FIGS. 1–2 illustrate, respectively, perspective and top views of a preferred embodiment of a therapeutic fingernail treatment device constructed and operated in accordance with the principles of the present invention.
Figure 2:
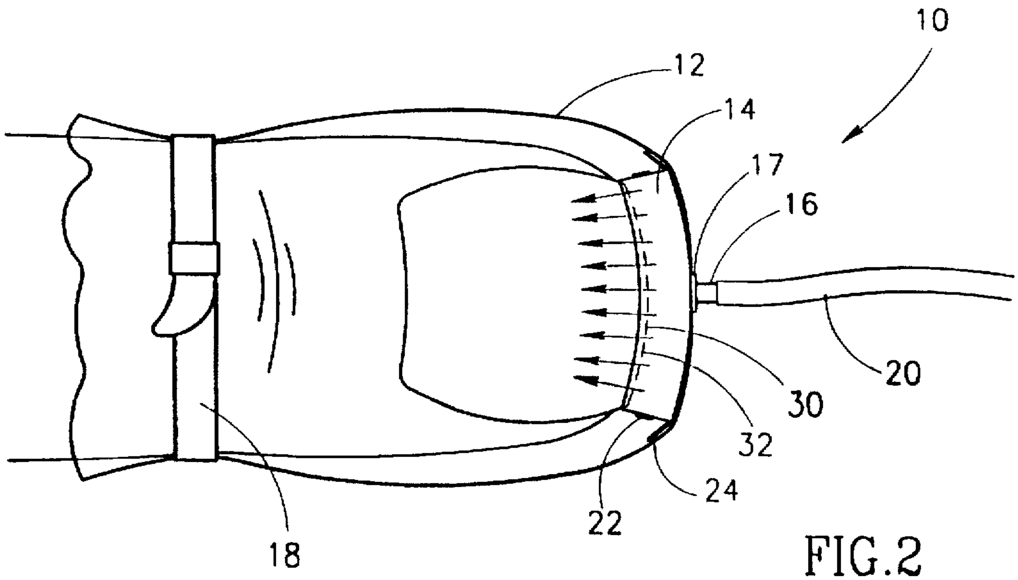

Referring now to FIGS. 1–2, there are illustrated, respectively, side and top views of the fingernail treatment device 10 constructed and operated in accordance with the principles of the present invention. Device 10 comprises an elastic sleeve 12, a spray jet 14 seated at an end of sleeve 12, with a threaded connection nipple 16 and locking nut 17 extending from spray jet 14 through the end of sleeve 12. A flexible clamp 18 is attached around the other end of sleeve 12, clamping it against the finger. Flexible clamp 18 may comprise a toothed strap which engages a locking tab mounted in a slidable buckle. Release of the locking tab enables the slidable buckle to be loosened so that flexible clamp 18 can be readjusted.

A flexible hose 20 is connected at one end to nipple 16, and at its other end to a flexible hand pump 36 via nipple 38. A one-way valve 40 mounted on an end of hand pump 36 enables it to regain its shape once depressed, to inflate and deflate sleeve 12. An electric pump can also be used, although this would increase the cost over the simple hand pump. On either side of spray jet 14 there is seated a fluid flow valve 22 (FIG. 2). An edge guard 24 attached at each side of spray jet 14 prevents elastic sleeve 12 from blocking the operation of flow valve 22.

Figure 3:
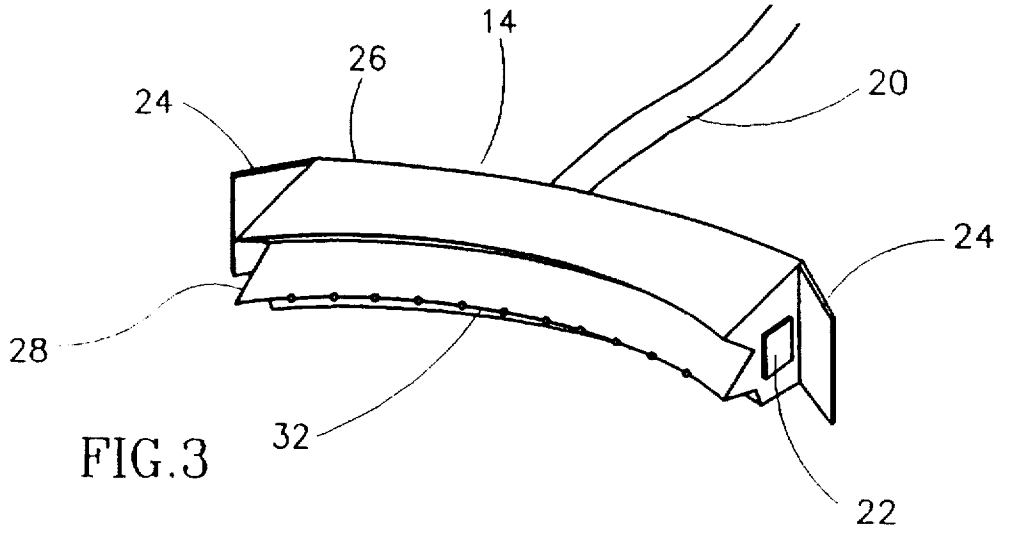
FIGS. 3–4 illustrate, respectively, perspective and top views of a spray jet utilized in the device of FIGS. 1–2.
Figure 4:
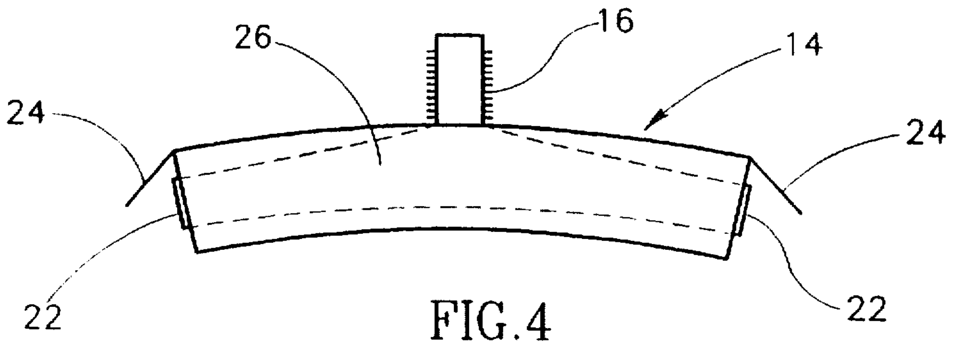

In FIGS. 3–4, there are shown, respectively, side perspective and top views of spray jet 14, featuring further construction details. Spray jet 14 is shaped as a curved housing 26, having a front face formed with a slot 28 designed to engage the edge of fingernail 30, as shown in FIGS. 1–2. The lower side of slot 28 is formed with a plurality of perforations 32 through which pass the active ingredients used in fingernail treatment. The curvature of housing 26 maintains even contact with edge 30. To position spray jet 14 correctly, fingernail edge 30 is placed in slot 28 while sleeve 12 is drawn tight, and fixed by clamp 18.

Figure 5A:
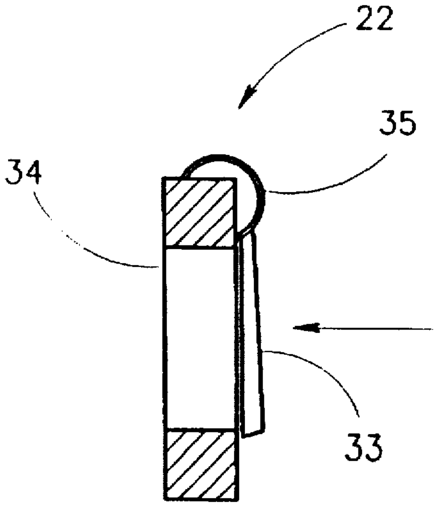
FIGS. 5*a–b* illustrate detailed views of a valve used in the spray jet of FIGS. 3–4.
Figure 5B:
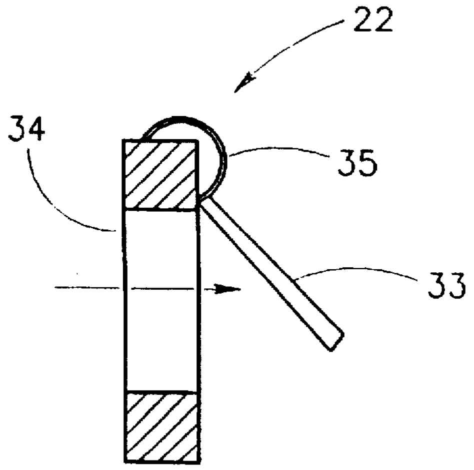

In FIGS. 5*a*–*b*, there are shown fluid flow valves 22 which are provided on the sides of curved housing 26 of spray jet 14. Each of valves 22 has a flap 33 mounted over the interior side of an opening 34 formed in the side of housing 26, and flaps 33 are spring-loaded under tension of springs 35 which are attached onto housing 26. Thus, valves 22 are normally closed. As described further herein, depending on the direction of fluid flow (arrows), valves 22 are open or shut to pass or block flow, by exposing or covering the interior side of openings 34.

Figure 6:
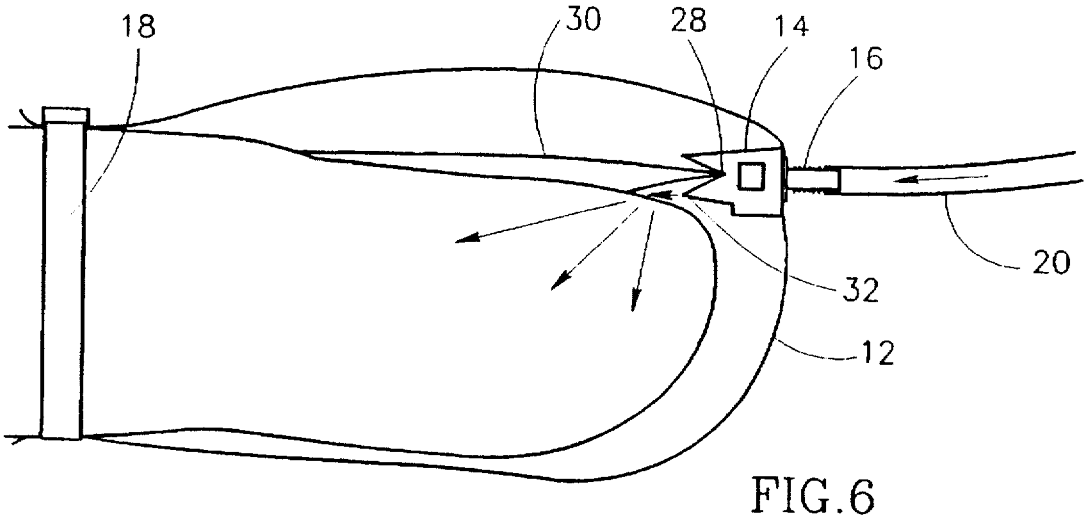
FIGS. 6–7 illustrate the operation of the fingernail treatment device during cyclical development of high and low pressure conditions of the sealed sleeve.
Figure 7:
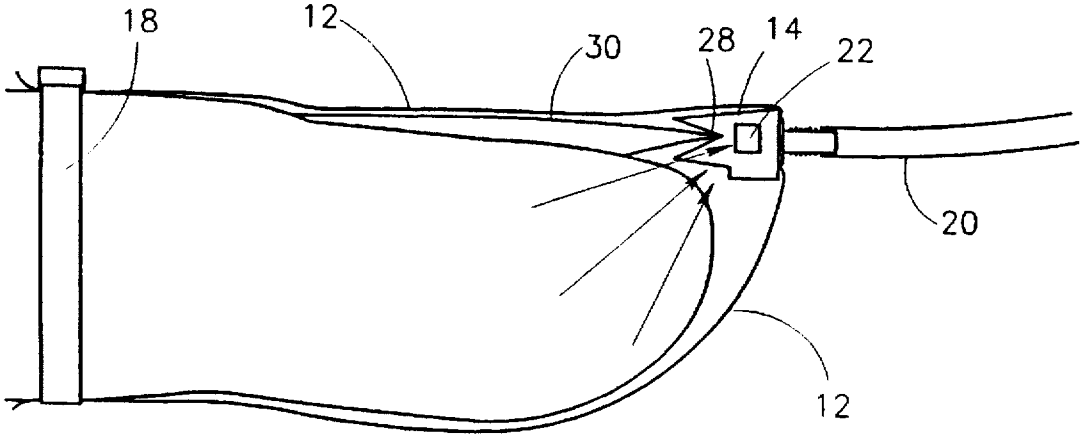

Referring now to FIGS. 6–7, sleeve 12 provides a sealed space at the end of the finger which enables active ingredients to be injected in cyclic fashion into the space between the fingernail 30 and the fingertip. Hose 20 is filled with active ingredients, and is connected to hand pump 36. The sleeve 12 is made of elastic material and is disposable. It is replaced by opening locking nut 17 and removing it. After replacing it with a new sleeve, locking nut 17 is tightened again on nipple 16 to seal sleeve 12 to spray jet 14.

The flexible clamp 18 on the finger permits sleeve 12 to be sealed, and relaxed if needed. Blood flow in the finger may be stopped, during operation of the device 10. Due to the variations in sizes of the fingers, the sleeve 12 size must be chosen accordingly. If several fingers are to be treated simultaneously, sleeve 12 can be chosen for this purpose, with an electric pump 37 used instead of hand pump 36, to increase pressure.

In operation, when hand pump 36 (not shown) is squeezed, active fluid ingredients are pumped into spray jet 14, and pass under pressure via perforations 32 into the space between the fingernail and fingertip (FIG. 6). Subjected to this pressure, elastic sleeve 12 inflates. Valves 22 remain closed during this portion of the cycle. In the portion of the cyclical operation of the pump causing suction within sleeve 12, the active ingredients are withdrawn and returned to hose 20 via the flow valves 22, which open inwardly within housing 26.

As elastic sleeve 12 relaxes and deflates to its initial size, it assists in returning active ingredient to hose 20. Edge guards 24 prevent elastic sleeve 12 from interfering with valves 22. With each cyclical inflation and deflation of sleeve 12, active ingredients contact the fingernail tip and are withdrawn. An optional mode of operation provides suction only in each cycle, to remove buildup of active ingredients in hose 20.

In summary, device 10 can be used to treat and eliminate fungus under the fingernail. Many advantages are provided over existing devices, especially by conservation of the quantity of active ingredients used, since these are recycled, by use of a sealed sleeve to eliminate wastage of ingredients.

The provision of a contoured spray jet 14 insures increased efficiency by providing good contact between the active ingredients and the entire fingernail area. In addition, the pressure developed within sealed sleeve 12 affords good impregnation of the active ingredients within the affected area.

Furthermore, device 10 can be provided in a compact design, and its operation does not require any special skill.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

I claim:

1. A device for therapeutic treatment of a fingernail, said device comprising:

means for enclosing the fingernail in sealed fashion; and nozzle means attached at an end of said enclosing means and facing the fingernail, said nozzle means being connected to a fluid source having means for reversibly pumping said fluid therethrough, and back to said fluid source, in cyclical fashion, such that said fluid periodically flows under the fingernail, and is withdrawn therefrom, providing therapeutic fingernail treatment.

2. The device of claim 1 wherein said enclosing means comprises an elastic sleeve for sealing over the end of a finger by a flexible clamp.

3. The device of claim 1 wherein said nozzle means comprises a spray jet having a concave contour facing the fingernail, for providing contact therewith along its length.

4. The device of claim 3 wherein said spray jet has perforations formed therein for passage of liquid therethrough.

5. The device of claim 1 wherein said nozzle means has valve means for directing said periodic flow of said fluid.

6. The device of claim 5 wherein said valve means comprises an opening in each side of said nozzle means, with an interior side of said opening having a spring-loaded, normally closed flap covering said opening, to block or enable fluid flow.

7. The device of claim 1 wherein said fluid source comprises a flexible hand pump partially filled with fluid in a flexible chamber thereof, depression of said chamber driving fluid flow into said device, and return via suction upon release.

8. The device of claim 1 wherein said fluid source comprises a fluid chamber connected to an electric pump.

9. A method of therapeutic fingernail treatment comprising the steps of:

enclosing a fingernail in a sealed fashion; and providing nozzle means facing said enclosed fingernail, said nozzle means being connected to a fluid source; and reversibly pumping said fluid through said nozzle means, and back to said fluid source, in cyclical fashion, such that said fluid periodically flows under said fingernail, and is withdrawn therefrom, providing therapeutic fingernail treatment.

10. The method of claim 9 wherein said reversible pumping step, said fluid periodically develops pressure in said fingernail enclosure and relaxes it to direct said fluid flow.

11. The method of claim 9 wherein during said reversible pumping step, said fluid exits said nozzle means via perforations formed therein and returns to said fluid source via nozzle valves.

12. The method of claim 9 wherein said reversible pumping step is performed by a hand pump having a one-way valve.

13. The method of claim 9 wherein said reversible pumping step is performed by an electric pump having a one-way valve.

14. The method of claim 9 wherein said enclosing step is performed by sealing said fingernail in a disposable elastic sleeve.

15. The method of claim 14 wherein said sealing step is performed by an adjustable, flexible clamp seated over said disposable sleeve for sealing it around a finger.

* * * * *